United States Patent [19]

Kim et al.

[11] Patent Number: 5,200,518

[45] Date of Patent: Apr. 6, 1993

[54] ANTI-INFLAMMATORY CARBOXYCYCLIC ACETAL PREGNANE DERIVATIVES

[75] Inventors: Hyun P. Kim; Kwan S. Sin; Chang M. Kim; Moon Y. Heo, all of Chuncheon, Rep. of Korea; Henry J. Lee, Tallahassee, Fla.

[73] Assignee: Kangweon National University, Chuncheon, Rep. of Korea

[21] Appl. No.: 658,542

[22] Filed: Feb. 21, 1991

[51] Int. Cl.$^5$ .............................................. C07J 71/00
[52] U.S. Cl. ...................................... 540/63; 540/31; 540/67; 540/70
[58] Field of Search ................... 549/432; 540/31, 63, 540/67, 70

[56] References Cited

U.S. PATENT DOCUMENTS 3,048,581  8/1962  Fried ..................................... 540/27

Primary Examiner—Nicky Chan
Attorney, Agent, or Firm—Arthur G. Yeager; Earl L. Tyner

[57] ABSTRACT

Compounds of the formula:

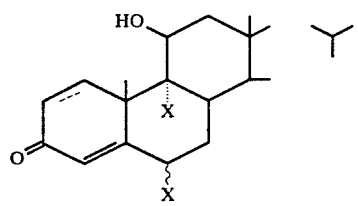

wherein
X is H, F, Cl, or $CH_3$ and Y is

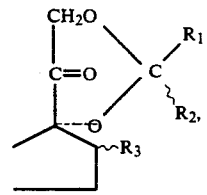

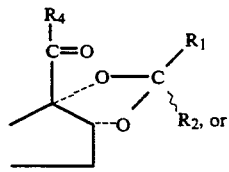

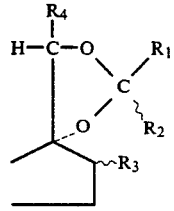

wherein
$R_1$ is H, alkyl of 1–5 carbon atoms, phenyl, or benzyl;
$R_2$ is $COOR_6$, $R_5$ $COOR_6$, or $R_5CONHR_6$;
$R_3$ is H, F, OH, or $CH_3$;
$R_4$ is $CH_2OH$, $CH_2OCOR_6$, $COOR_6$, or $CONHR_6$;
$R_5$ is alkyl of 1–3 carbon atoms;
$R_6$ is alkyl of 1–5 carbon atoms, or benzyl;
= represents a single or double bond;
∼ represents α-position, β-position, or a mixture of both α- and β-positions; and
— represents α-position;
and methods for preparing the same.

4 Claims, No Drawings

ANTI-INFLAMMATORY CARBOXYCYCLIC ACETAL PREGNANE DERIVATIVES

BACKGROUND OF THE INVENTION

Since hydrocortisone was found to possess anti-inflammatory activity in treating rheumatoid arthritis, numerous synthetic analogues of glucocorticoids have been used to treat inflammatory and/or immune malfunctional diseases.

Although the beneficial effects of natural semisynthetic glucocorticoids have been appreciated for over 40 years, the limiting factor in the use of corticosteroids for the chronic and/or high dose treatment have been their systemic side-effects. Continual research to eliminate these systemic side effects was carried out and one of the side-effects, salt-retaining activity, was successfully abrogated by the introduction of C-1,2 double bond and C-16 methyl or hydroxyl substitutions shown by prednisolone, dexamethasone, betamethasone and triamcinolone. However, little success has been achieved in separating the anti-inflammatory effect of steroids from their adverse side-effects mainly occurred by glucocorticoidal activity.

Therapeutic approaches such as dosage forms for local application, alternate day administration and concomitant protective therapy have been employed to reduce the adverse systemic effects of potent steroids. Although systemic effects are known to be reduced when conventional steroids are applied topically, the use of steroids in large quantities for prolonged periods results in toxic systemic side-effects and all clinically effective topical steroids have the potential to produce adverse effects. Among the patients using steroids, children are particularly prone to the systemic effects of local steroid application and suppression of pituitary-adrenal function including growth retardation has been reported.

One structural modification by Laurent et al. in U.S. Pat. No. 3,944,577 was introducing a 20-carboxyl ester group. These compounds showed reduced systemic effects, however, the anti-inflammatory potency was not sufficient.

Steroid derivatives as described in U.S. Pat. No. 4,762,919 to Lee employed a similar strategy of introducing a carboxylic ester group to the steroid molecule. Several of these compounds showed high anti-inflammatory activity with greatly reduced systemic side-effects, but the synthetic procedures to the final compounds were found to be difficult. Therefore, other improvements were needed to provide acceptance for the new compounds.

It is an object of this invention to provide novel pregnane derivatives having carboxyester and amide groups connected to the cyclic acetal side-chain at strategic 17,21-17,20- or 16,17- positions of steroid molecule as safer anti-inflammatory steroids. It is another object of this invention to provide more convenient procedures for the synthesis of such steroid derivatives. Other objects will appear in the more detailed description which follows.

BRIEF DESCRIPTION OF THE INVENTION

This invention relates to carboxycyclic acetal pregnane derivatives of the formula:

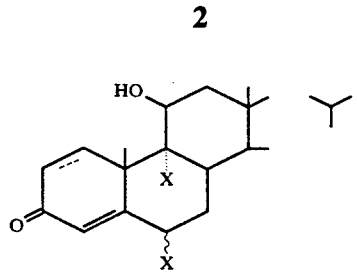

wherein
X is H, F, Cl, or $CH_3$;
and Y is

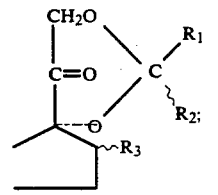

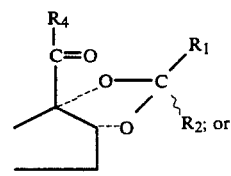

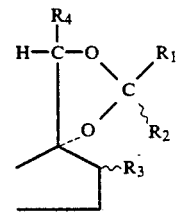

wherein
$R_1$ is H, alkyl of 1-5 carbon atoms, phenyl, or benzyl;
$R_2$ is $COOR_6$, $R_5COOR_6$, or $R_5CONHR_6$;
$R_3$ is H, F, OH, or $CH_3$;
$R_4$ is $CH_2OH$, $CH_2OCOR_6$, $COOR_6$, or $CONHR_6$;
$R_5$ is alkyl of 1-3 carbon atoms;
$R_6$ is alkyl of 1-5 carbon atoms or benzyl;
represents a single or double bond;
~ represents α-position, β-position or a mixture of both α-and β-positions; and
--- represents α-position.

In certain preferred embodiments of this invention, the derivatives can be represented by the formula:

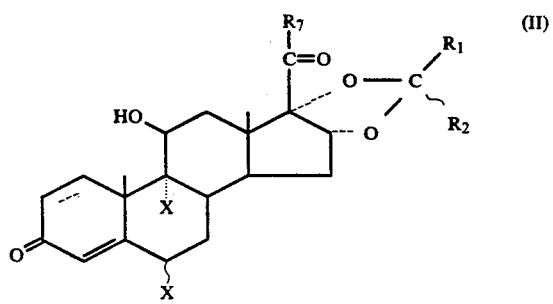

wherein X, $R_1$ and $R_2$ have the same meanings in Formula (I) above and $R_7$ is $CH_2OH$ or $CH_2OCOR_6$ where $R_6$ has the same meaning as in Formula (I).

DETAILED DESCRIPTION OF THE INVENTION

The compounds of this invention are described by three formulas given below.

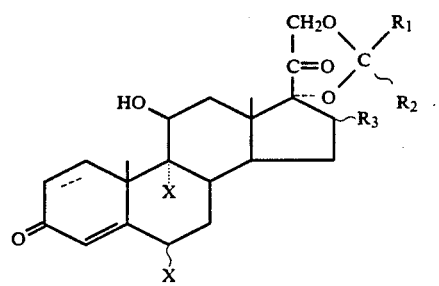
(III)

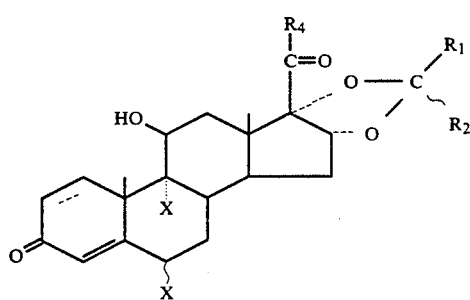
(IV)

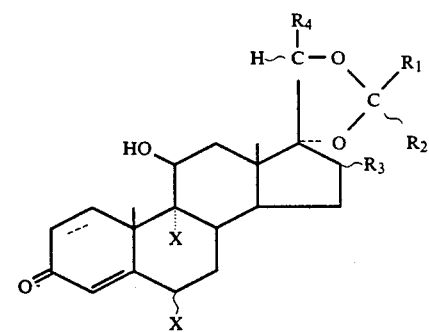
(V)

wherein all symbols have the same meaning as given for Formula (I) above.

These compounds all provide improved properties for use as an anti-inflammatory drug. The improvement resides principally in greater reductions in the adverse side-effects than have been observed in previously known compounds. All of the compounds are carboxycyclic acetal pregnane derivatives, and more specifically, the derivatives of cortisol or of prednisolone.

The most desirable of all of the compounds of this invention for anti-inflammatory uses with minimal systemic side-effects are those of the formula:

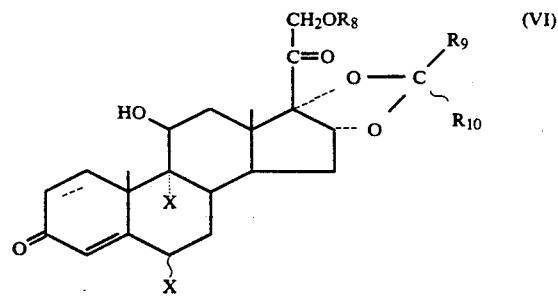
(VI)

wherein
x is H, F, Cl, or $CH_3$;
$R_8$ is H or $COR_6$;
$R_9$ is H, $CH_3$, phenyl, or benzyl;
$R_{10}$ is $COOR_{11}$, $CH_2COOR_{11}$, or $CH_2CH_2CH_2COOR_{11}$; and
$R_{11}$ is alkyl of 1–5 carbon atoms.

Among the specific compounds which are included in this invention are the following illustrative compounds. It is to be understood that the invention is not limited to these named compounds, but that these merely represent various substitutes which may be combined in many ways. The numbering of the compounds follows the structural formula given below:

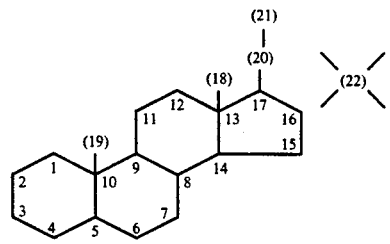

(22R)-11β-Hydroxy-3,20-dioxo-17,21-(methyl, methoxycarbonyl)methylenedioxy-1,4-pregnadiene;
(22S)-11β-Hydroxy-3,20-dioxo-17,21-(methoxycarbonylmethyl)methylenedioxy-4-pregnene;
(22S)-11β-Hydroxy-3,20-dioxo-17,21-(benzyl, methoxycarbonyl-n-propyl)methylenedioxy-1,4-pregnadiene;
(22R)-11β-Hydroxy-3,20-dioxo-17,21-(methoxycarbonyl)methylenedioxy-1,4-pregnadiene;
(22R)-9α-Fluoro-16α-methyl-11β-hydroxy-3,20-dioxo-17,21-(methyl, methoxycarbonyl-n-propyl) methylenedioxy-1,4-pregnadiene;
(22R)-11β,21-Dihydroxy-3,20-dioxo-16α,17-(methyl, ethoxycarbonyl-n-propyl) methylenedioxy-1,4-pregnadiene;
(22S)-11β,21-Dihydroxy-3,20-dioxo-16α,17-(N-n-propylaminocarbonyl-n-propyl)methylenedioxy-4-pregnene;
(22R)-11β,21-Dihydroxy-3,20-dioxo-16α,17-(methoxycarbonyl)methylenedioxy-4-pregnene;
(22R)-6α,9α-Difluoro-11β,21-dihydroxy-3,20-dioxo-16α,17-(methyl, methoxycarbonyl-n-propyl) methylenedioxy-1,4-pregnadiene;
(22S)-9α-Fluoro-11β,21-dihydroxy-3,20-dioxo-16α,17-(phenyl, methoxycarbonyl-n-propyl) methylenedioxy-1,4-pregnadiene;
(22R)-9α-Fluoro-11β,21-dihydroxy-3,20-dioxo-16α,17-(methyl, methoxycarbonyl methyl) methylenedioxy-1,4-pregnadiene;

(22R)-9α-Fluoro-11β,21-dihydroxy-3,20-dioxo-16α,17-(methyl,n-butyloxycarbonylmethyl)methylenedioxy-1,4-pregnadiene;

(22R)-9α-Fluoro-11β,21-dihydroxy-3,20-dioxo-16α,17-(methoxycarbonyl)methylenedioxy-1,4-pregnadiene;

(22R)-9α-Fluoro-11β,21-dihydroxy-3,20-dioxo-16α,17-(methyl, N-methylaminocarbonyl-n-propyl)methylenedioxy-1,4-pregnadiene;

(22R)-6α-Methyl-11β,21-dihydroxy-3,20-dioxo-16α,17-(methyl, methoxycarbonylmethyl)methylenedioxy-1,4-pregnadiene;

(22S)-11β-Hydroxy-21-acetoxy-3,20-dioxo-16α,17-(benzyl, methoxycarbonyl-n-propyl)methylenedioxy-1,4-pregnadiene;

(22R)-11β-Hydroxy-21-acetoxy-3,20-dioxo-16α,17-(methyl,methoxycarbonyl-methyl)methylenedioxy-1,4-pregnadiene;

n-Propyl (20R), (22R)-11β-hydroxy-3-oxo-17,20-(methyl,methoxycarbonyl-n-propyl)methylenedioxy-1,4pregnadien-21-oate;

Methyl (20S), (22R)-11β-hydroxy-3-oxo-17,20-(methyl,methoxycarbonyl-n-propyl)methylenedioxy-14-pregnadien-21-oate;

(20R), (22R)-21-(N-Methylamino)-11β-hydroxy-3,20-dioxo-17,20-(methyl,methoxycarbonyl-n-propyl)-methylenedioxy-4-pregnene;

(20R), (22R)-21-Acetoxy-11β-hydroxy-3-oxo-17,20-(methyl,methoxycarbonylmethyl)methylenedioxy-1,4-pregnadiene;

(20S), (22R)-21-acetoxy-11β-hydroxy-3-oxo-17,20-(methyl,methoxycarbonyl-n-propyl)methylenedioxy-4-pregnene.

The process for preparing carboxycyclic acetal pregnane derivatives of this invention cyclicized through the 17,21-positions proceeds as follows:

(1) Hydrocortisone or prednisolone or dexamethasone or betamethasone is reacted with an alkyl acetylalkanoate in a solution of dichloromethane or dioxane in the presence of catalytic amount of perchloric acid to produce the corresponding 17,21-carboxycyclic acetal pregnane derivatives, e.g., when hydrocortisone and methyl acetylformate are used the product is (I) 11β-hydroxy-3,20-dioxo-17,21-(methyl,methoxycarbonyl)-methylenedioxy-4-pregnane; when prednisolone and methyl acetylbutyrate are used the product is (II) 11β-hydroxy-3,20-dioxo-17,21-(methyl,methoxycarbonyl-n-propyl) methylenedioxy-1,4-pregnadiene; when dexamethasone and ethyl acetylacetate are used the product is (III) 9α-fluoro-11β-hydroxy-16α-methyl-3,20-dioxo-17,21-(methyl,ethoxycarbonylmethyl)methylenedioxy-1,4-pregnadiene;

(2) Hydrocortisone or prednisolone or dexamethasone or bethamethasone is reacted with an alkyl formylalkanoate in a solution of dichloromethane in the presence of catalytic amount of perchloric acid to produce the corresponding 17,21-carboxycyclic acetal pregnane derivatives, e.g., when hydrocortisone and methyl formylbutyrate are used the product is (IV) 11β-hydroxy-3,20-dioxo-17,21-(methoxycarbonyl-n-propyl) methylenedioxy-4-pregnene; when prednisolone and methyl formylacetate are used the product is (V) 11β-hydroxy-3,20-dioxo-17,21-(methoxycarbonylmethyl)methylenedioxy-1,4-pregnadiene.

The process for preparing carboxycyclic acetal pregnane derivatives of this invention cyclicized through the 16α, 17-positions proceeds as follows:

(1) Hydrocortisone or prednisolone is reacted with triethylorthoacetate and pyridine tosylate in benzene to synthesize a cyclic structure joining the 17- and 21-positions, e.g., (I) 11β-hydroxy-12,21-cyclocabonyloxy-3,20-dioxo-1,4-pregnadiene;

(2) (I) is reacted with sodium acetate buffer in methanol to break the cyclic structure and substitute an acetate group at the 17-position to produce, e.g., (II) 11β,21-dihydroxy-17-acetoxy-3,20-dioxo-1,4-pregnadiene;

(3) (II) is reacted with acetic anhydride in pyridine to incorporate the acetate group on the 21-position to produce, e.g., (III) 11β-hydroxy-17,21-diacetoxy-3,20-dioxo-1, 4-pregnadiene;

(4) (III) is reacted with potassium acetate in dimethylformamide to remove the 17-acetoxy group to produce, e.g., (IV) 11β-hydroxy-21-acetoxy-3,20-dioxo-1,4,16-pregnatriene;

(5) (IV) is reacted with osmium tetroxide to oxidize 16-unsaturated position to make vicinal-diol structure, e.g., to produce (V) 11β,16α, 17-trihydroxy-21-acetoxy-3,20-dioxo-1, 4-pregnadiene; and (V) is saponified with sodium hydroxide in methanol to produce, e.g., (VI) 11β,16α,17,21-tetrahydroxy-3, 3,20-dioxo-1,4-pregnadiene;

(6) (IV) is reacted with potassium permanganate to produce same (V), which is saponified to produce same (VI);

(7) (VI) or triamcinolone is reacted with an alkyl acetylalkanoate in a solution of dichloromethane in the presence of catalytic amount of perchloric acid to produce the corresponding 16α,17-carboxycyclic acetal pregnane derivatives, e.g., when (VI) and methyl acetylbutyrate are used the product is (VII) 11β,21-dihydroxy-3,20-dioxo-16α, 17-(methyl,methoxycarbonyl-n-propyl)methylenedioxy-1,4-pregnadiene; when triamcinolone and methyl acetylbutyrate are used the product is (VIII) 9α-fluoro-11β,21-dihydroxy-3, 20-dioxo-16α,17-methyl,methoxycarbonyl-n-propyl)methylenedioxy-1,4-pregnadiene; when triamcinolone and methyl acetylacetate are used the product is (IX) 9α-fluoro-11β,21-dihydroxy-3,20-dioxo-16α,17-17-(methyl,methoxycarbonylmethyl) methylenedioxy-1,4-pregnadiene; when triamcinolone and methyl acetylformate are used the product is (X) 9α-fluoro-11β,21-dihydroxy-3,20-dioxo-16α,17-(methyl,methoxycarbonyl)methylenedioxy-1,4-pregnadiene;

(8) (VI) or triamcinolone is reacted with an alkyl formylalkanoate in a solution of dichloromethane in the presence of catalytic amount of perchloric acid to produce the corresponding 16α,17-carboxycyclic acetal pregnane derivatives, e.g., when triamcinolone and methyl formylformate are used the product is (XI) 9α-fluoro-11β,21-dihydroxy-3,20-dioxo-16α, 17-(methoxycarbonyl)methylenedioxy-1,4-pregnadiene; when triamcinolone and ethyl formylformate are used the product is (XII) 9α-fluoro-11β,21-dihydroxy-3,20-dioxo-16α,17-(ethoxycarbonyl)methylenedioxy-1,4-pregnadiene;

(9) (X) is reacted with acetic anhydride in pyridine to produce, e.g., (XIII) 9α-fluoro-21-acetoxy-11β-hydroxy-3,20-dioxo-16α,17-(methyl,methoxycarbonyl)-methylenedioxy-1,4-pregnadiene;

(10) (VI) or triamcinolone is reacted with an alkyl benzoylalkanoate in a solution of dichloromethane and dioxane in the presence of catalytic amount of perchloric acid to produce the corresponding 16α,17-carboxycyclic acetal pregnane derivatives, e.g., when triamcinolone and methyl benzoylbutyrate are used the produce is (XIV) 9α-fluoro-11β,21-dihydroxy-3,20-dioxo- 16α,17-(phenyl,methoxycarbonyl-n-propyl) methylenedioxy-1,4-pregnadiene; when triamcinolone and methyl benzoylpropionate are used the produce is (XV) 9α-fluoro-11β, 21-dihydroxy-3,20-dioxo-16α,17-(phenyl,-methoxycarbonylethyl) methylenedioxy-1,4-pregnadiene;

(11) (VI) or triamcinolone is reacted with an acetylalkanoic acid in a solution of dichloromethane in the presence of catalytic amount of perchloric acid to produce the corresponding 16α,17-carboxycyclic acetal pregnane derivatives, e.g., when triamcinolone and acetylacetic acid are used the product is (XVI) 9α-fluoro-11β,21-dihydroxy-3,20-dioxo-16α, 17-(methyl, carboxylicmethyl)methylenedioxy-1,4-pregnadiene; when triamcinolone and acetylbutyric acid are used the product is (XVII) 9α-fluoro-11β,21-dihydroxy-3,20-dioxo-16α,17-(methyl, carboxylic-n-propyl)methylenedioxy-1,4-pregnadiene; (XVII) is reacted with diazomethane to produce same (VIII);

(12) (VI) or triamcinolone is reacted with an acetylcarboxamide in a solution of dichloromethane in the presence of catalytic amount of perchloric acid to produce the corresponding 16α,17-aminocarbonylcyclic acetal pregnane derivatives, e.g., when triamcinolone and acetylpropyl (N-methyl) carboxamide are used the product is (XVIII) 9α-fluoro-11β, 21-dihydroxy-3,20-dioxo-16α,17-(methyl,methylaminocarbonyl-n-propyl)-methylenedioxy-1,4-pregnadiene;

The process for preparing carboxycyclic acetal pregnane derivatives of this invention cyclicized through the 17,20-positions proceeds as follows:

(1) Hydrocortisone or prednisolone with 20-hydroxy and 21-acetoxy groups are known, e.g., (I) (20R)-21-acetoxy-11β, 17,20-trihydroxy-3-oxo-1,4-pregnadiene; and (I) is reacted with an alkyl acetylalkanoate in the presence of perchloric acid to produce the corresponding 17,20-carboxycyclic acetal pregnane derivatives, e.g., when methyl acetylbutyrate is used the product is (II) (20R)-21-acetoxy-11β-hydroxy-3-oxo-17,20-(methyl,methoxycarbonyl-n-propyl)methylenedioxy-1,4-pregnadiene;

(2) Hydrocortisone or prednisolone with 20-hydroxy and 20-carboxy groups are known, e.g., (III) methyl (20R)-11β,17, 20-trihydroxy-3-oxo-1,4-pregnadien-21-oate; and (III) is reacted with an alkyl acetylalkanoate or alkyl formylalkanoate in the presence of perchloric acid to produce the corresponding 17,20-carboxycyclic acetal pregnane derivatives, e.g., when methyl acetylbutyrate is used the product is (IV) methyl (20R)-11β-hydroxy-3-oxo-17,20-(methyl,methoxycarbonyl-n-propyl)methylenedioxy-1,4-pregnadien-21-oate; when methyl formylformate is used the product is (V) methyl (20R)-11β-hydroxy-3-oxo-17,20-(methoxycarbonyl)-methylenedioxy-1,4-pregnadien-21-oate;

(3) Prednisolone with 20-hydroxy and 20-carboxamide groups are known, e.g., (VI) (20R)-21-(n-.propylamino)-11β,17, 20-trihydroxy-3,21-dioxo-1,4-pregnadiene; and (VI) is reacted with an alkyl acetylalkanoate or alkyl formylalkanoate in the presence of catalytic amount of perchloric acid to produce the corresponding 17,20-carboxycyclic acetal pregnane derivatives, e.g., when methyl acetylbutyrate is used the product is (VII) (20R)-21-(n-propylamino)-11β-hydroxy-3,21-dioxo-17,20-(methyl, methoxycarbony-n-propyl)methylenedioxy-1,4-pregnadiene.

The process for separating each isomer at C-22 position (22R- or 22S-) of the products in this invention is as follows:

(1) The corresponding (22RS)-isomeric mixture described above, obtained from the procedure for preparing 17,21-carboxycyclic acetal pregnane derivatives or from the procedure for preparing 16,17-carboxycyclic acetal pregnane derivatives or from the procedure for preparing 17,20-carboxycyclic acetal pregnane derivatives is dissolved in small amount of chloroform or chloroform:methanol mixture and applied to silica gel comumn. Elution using chloroform:methanol mixture as a mobile phase give each isomer. When each isomer is not pure from above procedure, the repeated crystallization is used. In several cases, the preparative HPLC separation is used using methanol and water mixture as a mobile phase.

In the following examples, there are illustrations of the above procedures. Part and percentages are by weight unless otherwise specified. Temperatures are in degrees Centigrade unless otherwise specified. Purity of the compounds was checked with TLC and HPLC. The specific identification of the α- or β- or R- or S-isomer is not intended to eliminate the other isomer from the illustration.

EXAMPLE 1

1 g of prednisolone was dissolved in 15 ml of acetone and 5 drops of perchloric acid were added. After 1 day with stirring at room temperature, 400 ml of dichloromethane was added and washed with 500 ml of distilled water twice. The organics was dried over anhydrous sodium sulfate. After evaporation, the product was applied to column chromatography on silica gel (70–230 mesh). Elution with chloroform:methanol (95:5) as a mobile phase gave 280 mg of 11β-hydroxy-3,20-dioxo-17,21-isopropylidenedioxy-1,4-pregnadiene. m.p.=242°–246° C.

EXAMPLE 2

1 g of triamcinolone is dissolved in 20 ml of dichloromethane, and 200 mg of methyl acetylbutyrate and 5 drops of perchloric acid were added. After 5 hrs with stirring at room temperature, 2% NaHCO$_3$ solution was added to neutralize the solution. The solution was washed twice with 800 ml of distilled water. After drying the organics over anhydrous sodium sulfate, the organics was evaporated to give oilic product. The oilic product was purified with silica gel column using chloroform:methanol (9:1) as a mobile phase. The corresponding fractions were obtained and evaporated to give 22R- and 22S-mixture (12:1) of 9α-fluoro-11β,21-dihydroxy-3, 20-dioxo-16α,17-(methyl,methoxycarbonyl-n-propyl)methylenedioxy-1,4-pregnadiene as a white foam (680 mg) based on the HPLC and NMR peaks.

To separate each isomer, the above R,S mixture dissolved in chloroform was rechromatographed to silica gel column using chloroform:methanol (95:5) as a mobile phase. Two fractions were pooled. The fraction eluted earlier having less polar compound was evaporated and crystallized from acetone-hexane mixture to give (22R)-9α-fluoro-11β,21-dihydroxy-3,20-dioxo-16α17-(methyl,methoxycarbonyl-n-propyl)methylenedioxy-1,4-pregnadiene (242 mg) as a white prism. m.p.=174°–178° C., $^1$H-NMR (CDCl$_3$) δ0.89(s,3H,13-CH$_3$), 1.10(s,3H,22-CH$_3$), 1.55(s,3H,10-CH$_3$), 3.60(s,3H,—COOCH$_3$), 4.17-4.65(m,3H,11-H and 20-CH$_2$O-), 5.06(m,1H,16-H), 6.12(m,1H,4-H), 6.35(m,1H,2-H), 7.22(d,1H,1-H). The second fraction eluted later having more polar compounds gave 22R- and 22S-mixture (1:3) of 9α-fluoro-11β,21-dihydroxy-3,20-dioxo-16α,17-(methyl,methoxycarbonyl-n-propyl)methylenedioxy-1,4 pregnadiene (80 mg), which was subjected to preparative HPLC using methanol:water (65:35) as a mobile phase to give (22S)-9α-fluoro-11β,21-dihydroxy-3,20-dioxo-16α,17-methyl,methoxycarbonyl-n-propyl)methylenedioxy-1, 4-pregnadiene (18 mg) as white foams, $^1$H-NMR (CDCl$_3$) δ0.89 (s,3H,13-CH$_3$), 1.38(s,3H,22-CH$_3$), 1.55(s,3H,10-CH$_3$). 3.65(s, 3H,—COOCH$_3$), 4.17–4.65(m,3H,11-H and 20-CH$_2$O-), 5.06(m,1H, 16-H), 6.12(m,1H,4-H), 6.35(m,1H,2-H), 7.22(d,1H,1-H).

EXAMPLE 3

1 g of triamcinolone is dissolved in 15 ml of dioxane and 200 mg of methyl acetylacetate and 5 drops of perchloric acid were added. After 1 day of stirring at room temperature, the solution was neutralized and extracted with 500 ml of dichloromethane. After drying over anhydrous sodium sulfate, the organics was evaporated and subjected to silica gel column chromatography using chloroform:methanol (9:1) as an eluate. The fraction corresponding ester derivatives were pooled and evaporated to dryness which contained small portions of triamcinolone acetonide due to the decarboxylation of ester during reaction. To remove triamcinolone acetonide, the product was rechromatographed with silica gel column. Elution with chloroform:MeOH (95:5) and recrystalligation from acetone gave 380 mg of (22R)-9α-fluoro-11β,21-dihydroxy-3,20-dioxo-16α,17-(methyl,methoxy carbonylmethyl)methylenedioxy-1,4-pregnadiene as a white prism. $^1$H-NMR (CDCl$_3$) δ0.89(s,3H,13-CH$_3$), 1.26(s,3H,22-CH$_3$), 1.56(s,3H,10-CH$_3$), 2.73(s,2H,22-CH$_2$CO-), 3.65(s,3H,-COOCH$_3$), 4.20–4.67(m,3H,11-H and 20-CH$_2$CO-), 5.11(m,1H,16-H), 6.18(m,1H,4-H), 6.32(d,1H,2-H), 7.27(d,1H,1-H).

EXAMPLE 4

Prednisolone (50 g) was dissolved in benzene (1,000 ml) and triethylorthoacetate (50 ml) and pyridine tosylate (1.25 g) were added. After distillation for 1.5 hrs, the solution was stored in refrigerator to give colorless cubic crystal (95 g). Recrystallization twice from benzene gave known pure prednisolone-17,21-ethyl orthoacetate as a colorless needle (54 g), m.p.=188°-189° C.

EXAMPLE 5

To a solution (50 g) of the product of Example 4 in 700 ml of methanol, 400 ml of 0.1N sodium acetate buffer was added. After refluxing for 15 hrs, methanol was evaporated. The residue was extracted with 500 ml of ethyl acetate. After drying over anhydrous sodium sulfate, the organics was evaporated to dryness. Recrystallization from acetone gave 24 g of prednisolone-17-acetate as a colorless hexagonal, m.p.=223°-224° C. $^1$H-NMR (CDCl$_3$) δ0.98(s,3H,13-CH$_3$), 1.45 (s,3H,10-CH$_3$), 2.04(s,3H,17-Ac), 3.05(m,1H,21-OH), 4.2–4.4(m,2H,20-CH$_2$O-), 4.52(m,1H,11-H), 6.04(s,1H,4-H), 6.29(dd,1H,J=10 and 2 Hz,2-H),7.25(d,1H,J=10 Hz,1-H).

To a solution of prednisolone-17-acetate (10 g) in 30 ml of pyridine, acetic anhydride (4 ml) was added. After 2 hrs at room temperature, 0.5N HCl (150 ml) was added. Extraction with ethyl acetate, washing with water and evaporation gave yellow oil. crystallization from acetone-hexane mixture gave 7.1 g of prednisolone-17,21-diacetate as a colorless hexagonal, m.p.=99.5°-100.5° C., 190°-191° C.

EXAMPLE 6

To a solution of prednisolone-17,21-diacetate (7 g) in 100 ml of dimethylformamide, anhydrous potassium acetate (10 g) was added and reaction was continued at 105°-108° C. under N$_2$ for 6 hrs. After cooling down, the solution was poured onto ice-water (1,000 ml). After filtering, the filter cake was dissolved in ethyl acetate (300 ml), dried on anhydrous sodium sulfate and evaporated. Recrystallization from acetone gave 4.8 g of 21-acetoxy-11β-hydroxy-1,4,16-pregnatriene (Product 6A) as a yellowish long cubic, m.p.=203°-205° C. $^1$H-NMR (CDCl$_3$) δ1.25(s,3H,13-CH$_3$), 1.48(s,3H,10-CH$_3$), 2.18(s,3H,21-Ac), 4.40(m,1H,11-H), 4.83–5.06(m,2H,20-CH$_2$O-), 6.02(s,1H,4-H), 6.28(dd,1H,J=10 and 2 Hz,2-H), 6.74(m,1H,16-H), 7.30(d,1H,J=10 Hz,1-H).

To a solution of above product (100 mg) in methanol (10 ml) was added 4N NaOH (0.1 ml). Reaction was continued in ice-bath for 15 min. Distilled water (200 ml) was added and extracted with 300 ml of dichloromethane. After drying over anhydrous sodium sulfate, the organics were evaporated. Recrystallization from acetone gave 57 mg of 11β,21-dihydroxy-1,4,16-pregnatriene (Product 6B) as a yellowish needle, m.p.=213°-215° C. $^1$H-NMR (CDCl$_3$) δ1.25(s,3H,13-CH$_3$), 1.49(s,3H,10-CH$_3$), 4.35–4.55(m,3H,20-CH$_2$O- and 11-H), 6.02(s,1H,4H), 6.28(dd,1H,J=10 and 2 Hz,2-H), 6.73(m,1H,16-H), 7.32(d,1H,J=10 Hz,1-H).

EXAMPLE 7

To a solution of a product of Example 6 (Product 6A), 1 g, in 20 ml ethanol, 30 mg of potassium permanganate and 13 mg of MgSO$_4$ dissolved in 5 ml distilled water were added. After stirring at room temperature for 18 hrs, the solution was filtered and filtrate was extracted with 200 ml of dichloromethane. After drying on anhydrous sodium sulfate, the organics was evaporated. The dried residue dissolved in small amount of chloroform:MeOH (9:1) was poured onto the silica gel column. Chloroform:MeOH (9:1) was used as a mobile phase. The pooled fractions were evaporated to give 380 mg of 21-acetoxy-11β,16α,17-trihydroxy-3,20-dioxo-1,4-pregnadiene (Product 7A), which was saponified with methanolic sodium hydroxide solution in ice bath for 10 min and distilled water (200 ml) was added. After extracting with 300 ml of dichloromethane, the organics was dried over anhydrous sodium sulfate and evaporated to give 203 mg of 11β,16α,17,21-tetrahydroxy-3,20-dioxo-1,4-pregnadiene (Product 7B) as white form, $^1$H-NMR (CDCl$_3$) δ0.88(s,3H,13-CH$_3$), 1.45(s,3H,10-CH$_3$), 4.25–4.63(m,4H,20-CH$_2$O-, 11-H and 16H), 5.74(m,1H,16-H), 6.01(s,1H,4-H), 6.26(dd,1H,J=10 and 2 Hz,2-H), 7.21(d,1H,J=10 Hz,1-H)

EXAMPLE 8

To a solution of the Product of Example 7 (Product 7B), 180 mg, in 10 ml of dichloromethane, methyl acetylbutyrate (1 ml) and 3 drops of perchloric acid were added. The reaction was continued until the solution was clear. After neutralizing the solution with 2% NaHCO$_3$, the mixture was extracted with dichloromethane (200 ml) and dried over anhydrous sodium sulfate. The organics was evaporated. The residue dissolved in small amount of chloroform was poured to silica gel column and eluted with chloroform:methanol (95:5) as a mobile phase. The eluate gave 86 mg of (22R)-11β,21-dihydroxy-3,20-dioxo-16α,17-(methyl,-methoxycarbonyl-n-propyl)methylenedioxy-1,4-pregnadiene, $^1$H-NMR (CDCl$_3$) δ 0.88(s,3H,13-CH$_3$), 1.10(s,3H,22-CH$_3$), 1.45(s,3H,10-CH$_3$), 3.61(s,3H,-COOCH$_3$), 4.18–4.02(m,3H,20-CH$_2$O- and 11-H), 5.05(m,1H,16-H), 6.03(s,1H,4-H), 6.28(dd,1H,J=10 and 2 Hz, 2-H), 7.23(d,1H,J=10 Hz,1-H).

EXAMPLE 9

Prednisolone (10 g) was dissolved in 750 ml of methanol and 2.25 g cupric acetate in 750 ml of methanol was added. The solution was mixed and set aside for 20 min. While stirring, the reaction was continued with airation for 1 weak. After adding 500 ml of 0.1% NaHCO$_3$ solution containing 4.5 g EDTA, methanol was evaporated under vacuum. The solution was extracted with ethyl acetate (1,000 ml), dried on anhydrous sodium sulfate and evaporated to dryness (7.5 g). The residue was dissolved in 150 ml methanol and 375 ml water containing 3.75 g NaHSO3 was added. After refluxing for 1 hour, water was evaporated and the residue was extracted with ethyl acetate (500 ml), washed with distilled water, dried on sodium sulfate and evaporated to dryness (3.5 g), which was purified with silica gel column with acetone:dichloromethane:hexane (3:2:5) as a mobile phase. The pooled fraction was evaporated to dryness. Recrystallization four times from methanol gave 1.1 g of methyl (20R)-11β,17,20-trihydroxy-3-oxo-1,4-pregnadien-21-oate (Product 9A) as a colorless platelet, m.p.=254°–255° C., $^1$H-NMR (Me$_2$SO-d$_6$) δ1.05(s,3H,13-CH$_3$), 1.40(s,3H,10-CH$_3$), 3.62(s,3H,21-OCH$_3$), 4.06(s,1H,20-H), 4.21(m,1H,11-H), 5.91(s,1H,4-H), 6.15(dd,1H,J=10 and 2 Hz,2-H), 7.32(d,1H,J=10 Hz,1-H); MS, m/e 390(M+). The combined remaining solution was evaporated. After dissolving in small amount of methanol, the solution was subjected to preparative HPLC using methanol:water (6:4) as a mobile phase. The eluate was evaporated and crystallized to give 0.8 g of methyl (20S)-11β,17,20-trihydroxy-3-oxo-1,4-pregnadien-21-oate (Product 9B) as a white prism, m.p.=171°– 173° C. $^1$H-NMR (CDCl$_3$) δ1.15(s,3H,13-CH$_3$), 1.45(s,3H,10-CH$_3$), 3.31(s,3H,21-OCH$_3$), 4.36(s,1H,20-H), 4.43(m,1H,11-H), 6.01(s,1H,4-H), 6.28(dd,1H,J=10 and 2 Hz,2-H), 7.28(d,1H,J=10 Hz,1-H); MS, m/e 390(M+).

EXAMPLE 10

To a solution of the product of Example 9 (Product 9A), 500 mg, in methanol (50 ml), 1N NaOH (1 ml) was added. After 20 min in ice bath, the mixture was neutrlized with 0.1N HCl and 300 ml of distilled water was added. After extracting with ethyl acetate (300 ml), the organics was evaporated and recrystallization from methanol gave 360 mg of (20R)-11β,17,20-trihydroxy-3-oxo-1,4-pregnadien-21-oic acid as white prism, m.p.=213°–214° C. $^1$H-NMR (Me$_2$SO-6) δ1.03(s,3H,13-CH$_3$), 1.39(s,3H,10-CH$_3$), 3.94(s,1H,20-H), 4.19(m,1N,11-H), 5.90(s,1H,4-H), 6.13(dd,1H,J=10 and 2 Hz,2-H), 7.31(d,1H,J=10 Hz,2-H), 8.30(s,1H,20-COOH).

EXAMPLE 11

To a solution of a product of Example 10 (200 mg) in tetrahydrofuran (3 ml) and dichloromethane (30 ml) were added N,N'-dicyclohexylcarbodiimide (120 mg) and 1-hydroxybenzotriazole (80 mg) in tetrahydrofuran (3 ml). The reaction mixture was stirred at 4° C. for 24 hrs. After filtration, n-propylamine (60 mg) was added to the filtrate, and the reaction was continued at 4° C. After 24 hrs, the mixture was diluted with dichloromethane (300 ml) and dried over anhydrous sodium sulfate, followed by evaporation. The residue dissolved in methanol was applied to silica gel column and eluted with chloroform:methanol (9:1) as a mobile phase. Recrystallization from acetone-hexane gave 130 mg of (20R)-21-(n-propylamino)-11β,17,20-trihydroxy-3,21-dioxo-1,4-pregnadiene, m.p.=251°–253° C. $^1$H-NMR (CDCl$_3$) δ0.94(t,3H, J=6 Hz,NHCH$_2$CH$_2$CH$_3$), 1.15(s,3H,13-CH$_3$), 1.45(s,3H,10-CH$_3$), 3.2(m,2H,NHCH$_2$-), 4.06(s,1H,20-H), 4.39(m,1H,11-H), 6.0(s,1H,4-H), 6.25(dd,1H,J=10 and 2 Hz,2-H), 6.9(m,1H,NH), 7.31(d,1H,J=10 Hz,1-H).

EXAMPLE 12

To a solution of the product of example 9 (Product 9B), 300 mg, in dichloromethane (20 ml), methyl acetobutylate (0.5 ml) and 5 drops of percloric acid were added. After 3 hrs with stirring at 50° C., distilled water (200 ml) was added, extracted with dichloromethane (200 ml) and the organics was dried over anhydrous sodium sulfate. After evaporation, the residue dissolved in small amount of chloroform and methanol was applied to silica gel column and eluted with chloroform:methanol (95:5). Eluate combined gave 88 mg of methyl (20S)-11β-3-oxo-17,20-(methyl, methoxycarbonyl-n-propyl) methylendi-oxy-1,4-pregnadien-21-oate. $^1$H-NMR (CDCl$_3$) δ1.07(s,3H,13-CH$_3$), 1.29(s,3H,22-CH$_3$), 1.47(s,3H,10-CH$_3$), 3.66(s,3H,-CH$_2$COOCH$_3$), 3.77(s,3H,20-COOCH$_3$), 4.54(m,2H,11-H and 20-H), 6.02(s,1H,4-H), 6.27(dd,1H,J=10 and 2 Hz,2-H), 7.26(d,1H,J=10 Hz,1-H).

EXAMPLE 13

Triamcinolone (400 mg) was dissolved in 10 ml of dichloromethane and 5 ml of dioxane. Methyl benzoylbutyrate (60 mg) and 5 drops of perchloric acid was added. After 5 hrs at room temperature with stirring, the reaction mixture was poured to 300 ml of distilled water and extracted with dichloromethane (500 ml). After drying on anhydrous sodium sulfate, the organics was evaporated to dryness. The residue dissolved in small amount of chloroform was purified with silica gel column using chloroform:methanol (95:5) as a mobile phase. The pooled fraction eluted was evaporated to give 22(R,S) mixture of 22R:22S (1.5:1) based on NMR peak intensities, 9α-fluoro-11β,21-dihydroxy-3,20-dioxo-16α,17-(phenyl,methoxycarbonyl-n-propyl)methylenedioxy-1,4-pregnadiene (207 mg) as white foam. $^1$H-NMR (CDCl$_3$) δ0.89 and 1.17(3H,13-CH$_3$), 1.55(s,3H,10-CH$_3$), 3.61 and 3.65(3H,-COOCH$_3$), 4.10–4.92(m,3H,11-H and 20-CH$_2$O-), 5.34(m,1H,16-H), 6.12(s,1H,4-H), 6.33(dd,1H,2-H), 7.06–7.97(m,6H,1-H and -C$_6$H$_5$).

EXAMPLE 14

Compounds of this invention were tested for pharmacological evaluation. The following procedures were employed. Male Sprague-Dawley rats weighing 120–140 g and male ICR mice (23–28 g) were maintained on standard laboratory chow with water ad libitum and kept under controlled condition for one week prior to their use. Cotton pellet weighing 35±1 mg cut from dental rolls were impregnated with steroid solution in acetone (0.2 ml each) and the solvent was removed by evaporation. The cotton pellets were subsequently injected with 0.2 ml aqueous solution of antibiotics (1 mg penicillie G and 1.3 mg dihydrostreptomycin/ml). Two cotton pellets were implanted s.c., one in each axilla of the rat under light ether anethesia, one of which contained steroid solution and the other one was only received antibiotic solution. Ganuloma inhibition of the pellet containing only antibiotic solution was considered as systemic effects. Seven days later, the animals were sacrificed and the pellets were removed, dried at 37° C. for 4 days and weighed. The increment in dry weight (difference between the initial and final pellet weight) is taken as a measure of granuloma formation. The results are shown in Table 1.

TABLE 1

| COMPOUND | DOSAGE mg/cotton pellet | DRY WT. OF GRANULOMA mg. | GRANULOMA INHIBITON % | RELATIVE THYMUS WT. mg/100 g B.W. |
|---|---|---|---|---|
| None (Control) | 0.0 | 49.0 ± 5.2 | — | 282.6 ± 16.6 |
| Prednisolone | 2.5 | 20.1 ± 2.3 | 59.0 | 167.2 ± 12.3 |
|  | 0.0 | 24.2 ± 1.7 | 50.6 |  |
| Prednisolone | 1.0 | 24.9 ± 1.8 | 49.2 | 245.7 ± 15.5 |
|  | 0.0 | 30.2 ± 2.6 | 38.4 |  |
| Triamcinolone | 2.5 | 27.3 ± 3.9 | 44.3 | 246.2 ± 21.3 |
|  | 0.0 | 28.2 ± 4.4 | 42.4 |  |
| Triamcinolone | 1.0 | 32.7 ± 1.6 | 33.3 | 251.6 ± 8.8 |
|  | 0.0 | 40.3 ± 3.1 | 17.8 |  |
| Product of Example 2(22R) | 2.5 | 25.3 ± 5.6 | 48.4 | 268.3 ± 11.6 |
|  | 0.0 | 41.0 ± 3.7 | 16.3 |  |
| Product of Example 2(22R) | 1.0 | 27.5 ± 4.3 | 43.9 | 273.2 ± 16.2 |
|  | 0.0 | 44.7 ± 5.1 | 8.8 |  |
| Product of Example 2(22S) | 1.0 | 34.9 ± 2.6 | 28.8 | 269.1 ± 16.9 |
|  | 0.0 | 46.4 ± 4.8 | 5.3 |  |
| Product of Example 9(20R) | 2.5 | 37.7 ± 6.7 | 23.1 | 293.2 ± 20.6 |
|  | 0.0 | 51.3 ± 3.6 | −4.7 |  |
| Product of Example 9(20S) | 2.5 | 28.5 ± 3.9 | 41.8 | 264.8 ± 13.7 |
|  | 0.0 | 49.6 ± 5.4 | 1.2 |  |
| Product of Example 3 | 1.0 | 25.0 ± 1.3 | 49.0 | 279.9 ± 18.2 |
|  | 0.0 | 50.8 ± 5.8 | −3.7 |  |

For measuring topical activity of the derivative, the compounds (0.001–0.1 mg) in acetone (25 ul) were applied to the left ear of male ICR mice. After 30 min., 2.5% crotone oil (25 ul each) was applied to both ears of the mice. The ear thickness was measured with Flower precision microgage after 5 hrs and the difference between initial and final thickness was regared as edema formation. The results were shown in Table 2.

TABLE 2

| COMPOUND | DOSAGE mg/ear | EDEMA INHIBITION % |
|---|---|---|
| Croton oil (control) |  | — |
| Dexamethasone | 0.1 | 82 |
|  | 0.0 | 78 |
| Dexamethasone | 0.01 | 69 |
|  | 0.0 | 52 |
| Dexamethasone | 0.001 | 56 |
|  | 0.0 | 23 |
| Prednisolone | 0.1 | 70 |
|  | 0.0 | 67 |
| Prednisolone | 0.01 | 52 |
|  | 0.0 | 29 |
| Prednisolone | 0.001 | 43 |
|  | 0.0 | −2 |
| Product of Example 3 | 0.1 | 69 |
|  | 0.0 | 14 |
| Product of Example 3 | 0.01 | 58 |
|  | 0.0 | 3 |
| Product of Example 3 | 0.001 | 51 |
|  | 0.0 | 8 |

For evaluating the systemic thymolytic effect of the derivatives of this invention in mice through topical administration, the derivatives were applied to left ear of the male ICR mice. After 3 days, mice were sacrificed by cervical dislocation. The thymus tissues were excised and weighed. The results were shown in Table 3. When the derivatives were applied to ICR mice by subcutaneous route, the systemic thymolytic effects were shown in Table 4.

TABLE 3

| COMPOUND | DOSAGE mg | THYMUS REDUCTION % |
|---|---|---|
| Control |  | — |
| Dexamethasone | 0.1 | 43 |
|  | 0.05 | 39 |
|  | 0.01 | 21 |
| Prednisolone | 0.1 | 24 |
|  | 0.05 | 9 |
|  | 0.01 | −8 |
| Product of Example 3 | 0.1 | 0 |
|  | 0.05 | 2 |
|  | 0.01 | 0 |

TABLE 4

| COMPOUND | DOSAGE mg | THYMUS REDUCTION % |
|---|---|---|
| Control |  | — |
| Dexamethasone | 0.05 | 56 |
|  | 0.02 | 50 |
|  | 0.01 | 39 |
| Prednisolone | 0.07 | 35 |
|  | 0.05 | 27 |
| - | 0.02 | −8 |
| Product of Example 3 | 0.5 | 11 |
|  | 0.1 | 0 |
|  | 0.05 | 1 |

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. Carboxycyclic acetal pregnane derivative of the formula:

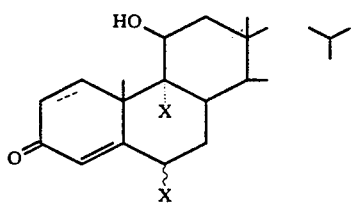

wherein
X is H, F, Cl, or CH₃;
and Y is

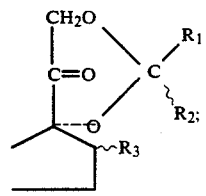

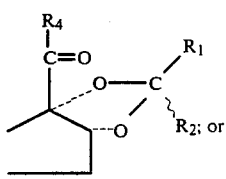

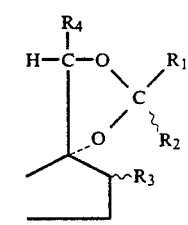

wherein
$R_1$ is H, alkyl of 1-5 carbon atoms, phenyl, or benzyl;
$R_2$ is $COOR_6$, or $R_5CONHR_6$;
$R_3$ is H, F, OH, or $CH_3$;
$R_4$ is $CH_2OH$, $CH_2OCOR_6$, $COOR_6$, or $CONHR_6$;
$R_5$ is alkyl of 1-3 carbon atoms;
$R_6$ is alkyl of 1-5 carbon atoms or benzyl;
⎓ represents a single or double bond;
∼ represents α-stereoconfiguration, β-stereoconfiguration or a mixture of both α- and β-stereoconfigurations; and
--- represents α-stereoconfiguration.

2. The derivative of claim 1 of the formula:

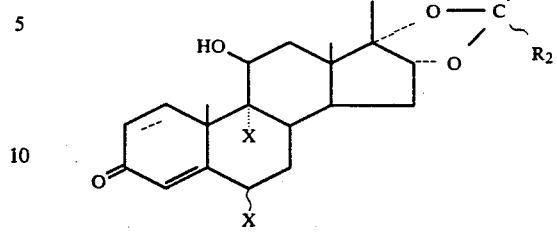

wherein X, $R_1$, $R_2$, and $R_4$ have the meanings given in claim 1.

3. The derivative of claim 2 of the formula:

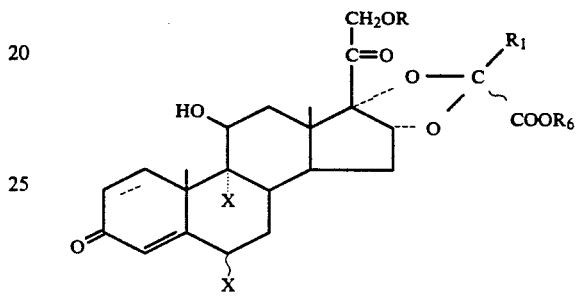

wherein
one X is H or F;
the remaining X is H, F, Cl, or $CH_3$;
R is H, or $COR_6$;
$R_1$ is H, $CH_3$, or phenyl; and
$R_5$ is an alkyl of 1-5 carbon atoms.

4. The derivative of claim 3 of the formula

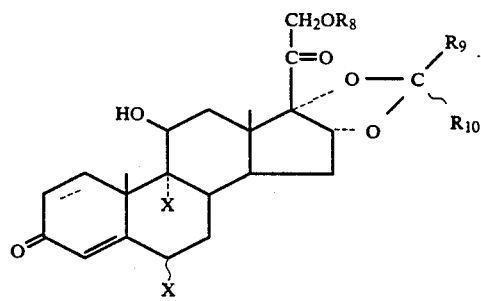

wherein
X is H, F, Cl, or $CH_3$
$X_8$ is H or $COR_6$
$R_9$ is H, $CH_3$, phenyl, or benzyl
$R_{10}$ is $COOR_{11}$; and
$R_{11}$ is alkyl of 1-5 carbon atoms.

* * * * *